US00PP14224P39

(12) United States Plant Patent

Jury et al.

(10) Patent No.: US PP14,224 P3
(45) Date of Patent: Oct. 14, 2003

(54) CORDYLINE PLANT NAMED 'JURRED'

(50) Latin Name: *Cordyline hybrida*
Varietal Denomination: JURred

(76) Inventors: Felix M. Jury, deceased, late of Waitara (NZ); Mark C. Jury, "Tikorangi" RD 43, Waitara, North Taranaki (NZ); Brett Gould, 136-138 Powderham Street, New Plymouth (NZ), executor of said Felix M. Jury, deceased; John C. Middleton, 136-138 Powderham Street, New Plymouth (NZ), executor of said Felix M. Jury, deceased ( * ) Notice: Subject to any disclaimer, the term of this patent is extended or adjusted under 35 U.S.C. 154(b) by 0 days.

(21) Appl. No.: 09/905,964

(22) Filed: Jul. 17, 2001

(65) Prior Publication Data

US 2003/0019004 P1 Jan. 23, 2003

(Under 37 CFR 1.47)

(51) Int. Cl.[7] ..... A01H 5/00
(52) U.S. Cl. ..... Plt./383
(58) Field of Search ..... Plt./370, 383

*Primary Examiner*—Bruce R. Campell
*Assistant Examiner*—Susan B. McCormick
(74) *Attorney, Agent, or Firm*—Foley & Lardner

(57) ABSTRACT

A new and distinct cultivar of Corydline plant named 'JURred' characterized by long and strappy leaves of deep burgundy red color, a small clump forming growth habit and flower spikes carrying numerous flowers of pale lilac color having a heavy jasmine-like fragrance.

2 Drawing Sheets

Latin name of the genus and species of the plant claimed: Cordyline hybrida.
Variety denomination: JURred.

BACKGROUND OF THE INVENTION

The present invention relates to a new and distinct cultivar of Cordyline plant botanically known as Cordyline hybrida, and referred to by the cultivar name 'JURred'.

The new cultivar was selected by the inventors, Felix M. Jury and Mark C. Jury, in Taranaki, New Zealand, and resulted from the cross pollination by hand of a Cordyline likely to have been a cross of *Cordyline banksii* and *Cordyline australis* 'Purple Tower' with pollen from *Cordyline pumilo* (unpatented parental cultivars). The resulting seeds were planted out and plants with desirable ornamental characteristics were selected. The variety was selected from the group of seedlings because of the unique color of its foliage. The variety was grown and divided from roots to produce further plants, the color in the foliage, height and clump forming nature remaining uniform and consistent during the growing period. Horticultural examination of selected units has demonstrated that the combination of characteristics as herein disclosed for 'JURred' are firmly fixed and are retained through successive generations of asexual reproduction.

The closest comparative cultivar to 'JURred' known to the applicant is *Cordyline pumilo. Cordyline pumilo* is a clump forming plant with dull brown-red foliage having narrower leaf (rarely exceeding 1.5 cm across) 'JURred' and only 40 to 70 cm long. The breeder of the seed is unknown.

BRIEF DESCRIPTION OF THE INVENTION

The following traits have been repeatedly observed and are determined to be basic characteristics of 'JURred' which, in combination, distinguish this Cordyline as a new and distinct cultivar:

1. long and strappy leaves of deep burgundy red color, RHS 200C;
2. a small clump forming growth habit;
3. flower spikes carrying numerous flowers of pale lilac RHS 85D; and
4. heavy jasmine-like fragrance.

'JURred' has not been observed under all possible environmental conditions. The phenotype of the new cultivar may vary significantly with variations in environment such as temperature, light intensity, and day length without any change in genotype. The following observations, measurements, and values describe the new cultivar as grown in Taranaki, New Zealand under conditions which approximate those generally used in commercial practice.

The new cultivar is a clump forming dwarf plant with distinctive deep burgundy red leaf color. The plant clumps over time, eventually forming bare stems up to 60 cm×4 cm, erect. Leaves 60 to 90 cm long×2 to 4 cm wide, narrowed above the base into channeled petiole; midrib prominent abaxially, at least proximally; margin slightly recurved. Flowers small (6 mm) on short pedicels. Pale lilac, darker externally; tepals narrow, recurved. Stigma shortly triffid. Fruit 4–5 mm diameter, globose purple black. Seeds 2 to 2.5 mm long, shining black.

The plant will form one good-sized crown in one year, and this crown will form offsets and have one flower spike in the second year. Inflorescence has up to one thousand flowers on the flower spike over a period of six to eight weeks. The flower spike is up to 100 cm in length and bears up to 1000 tiny flowers opening in succession over the six to eight week period. The flowers are symmetrical, have six petals, six stamens (white). The petals reflex right back and the stamens reflex partially. The flower exhibits yellow pollen and produces sets of up to six seeds per seed capsule, with only a partial set of seed. The flower has a heavy jasmine-like fragrance. The plant has no bracts and the flower is also sessile. The flower buds are small, oval oblong buds, 5 mm long, and are deep lilac on the outside opening to pale lilac on the inside. Petals reflex back on opening and after several days close again.

BRIEF DESCRIPTION OF THE DRAWINGS

The accompanying color photographs show the unique characteristics of the new cultivar including the distinctive leaf color, flower spikes and growth habit.

The first drawing shows the long strappy leaves of a plant of 'JURred' in its entirety.

The second drawing is a close-up of a flower spike of 'JURred' and its tiny flowers.

DETAILED BOTANICAL DESCRIPTION

Color references are made to The Royal Horticultural Society Colour Chart (R.H.S.) except where general colors of ordinary significance are used. Colors are approximate as color depends on horticultural practices such as light level and fertilization rate, among other things.

The age of the plant described is approximately 3 years old.

Parentage: *Cordyline banksii*×*Cordyline australis* 'Purple Tower' with pollen from *Cordyline pumilo.*
Method of breeding: Hand pollination.
Asexual propagation: Division of roots in Taranaki, New Zealand.
Plant habit:
- *Plant growth type.*—Clump forming.
- *Plant height.*—600 mm.
- *Plant width.*—120 mm.

Stem:
- *Stem diameter.*—25 mm.
- *Stem color.*—Purple brown (RHS 183C).

Leaf:
- *Leaf characteristics.*—Long and strappy.
- *Leaf length.*—60 to 90 cm.
- *Leaf color.*—Upper surface deep burgundy red (RHS 200C), under surface greyed-purple (RHS 187A).
- *Vein color and pattern.*—Grey-purple (RHS 184A), parallel pattern, raised.
- *Outer leaf sheath color.*—Purple brown (RHS 183C).
- *Leaf width.*—2 to 4 cm.
- *Margin.*—Entire.

Flower characteristics:
- *Bud.*—Shape: Ovate. Color: Purple brown (RHS 183C). Dimensions: 5 mm long, 2 mm wide.
- *Corolla.*—Shape: Star shaped. Size: 2 cm wide.
- *Flower profile upper.*—Flattened.
- *Flower profile lower.*—Flattened.
- *Sepal.*—Length: 4 mm. Color: Purple brown (RHS 183C). Extensions: Very weak.
- *Petals.*—Number: 6. Color: Pale lilac (RHS 85D). Size: Small. Width: 2 mm. Length: 5 mm. Arrangement: Not touching.
- *Pedicels.*—Length: 1 mm. Color: Purple brown (RHS 183C). Pedicel prickles: None.
- *Number of flowers.*—Inflorescence of many flowers (hundreds).
- *Floret length.*—5 mm.

Time of flowering: Spring/summer.
Length of flowering period: Medium, 6–8 weeks.
Color midzone outside RHS: Pale lilac (RHS 85D).
Midzone inside: Pale lilac (RHS 85D).
Margin inside: Pale lilac (RHS 85D).
Basal spot: None.
Reproductive organs:
- *Stamen.*—6, white. Filament color: White. Anther color: Yellow (RHS 4D). Pollen: Yellow.
- *Style color.*—Lilac (RHS 85D).

Seed vessel:
- *Size.*—Small 4 to 5 mm diameter globose.
- *Color.*—Deep green to purple black.

Seeds:
- *Size.*—2 to 2.5 mm long.
- *Color.*—Shining black.
- *Amount.*—6 per seed capsule.

Fragrance: Heavy jasmine-like fragrance.
Pests and diseases: Resistant to the cabbage tree moth.
Winter hardiness: To minus 5° C.
Drought/heat tolerance: Excellent.

We claim:

1. A new and distinct Cordyline plant named 'JURred' as illustrated and described.

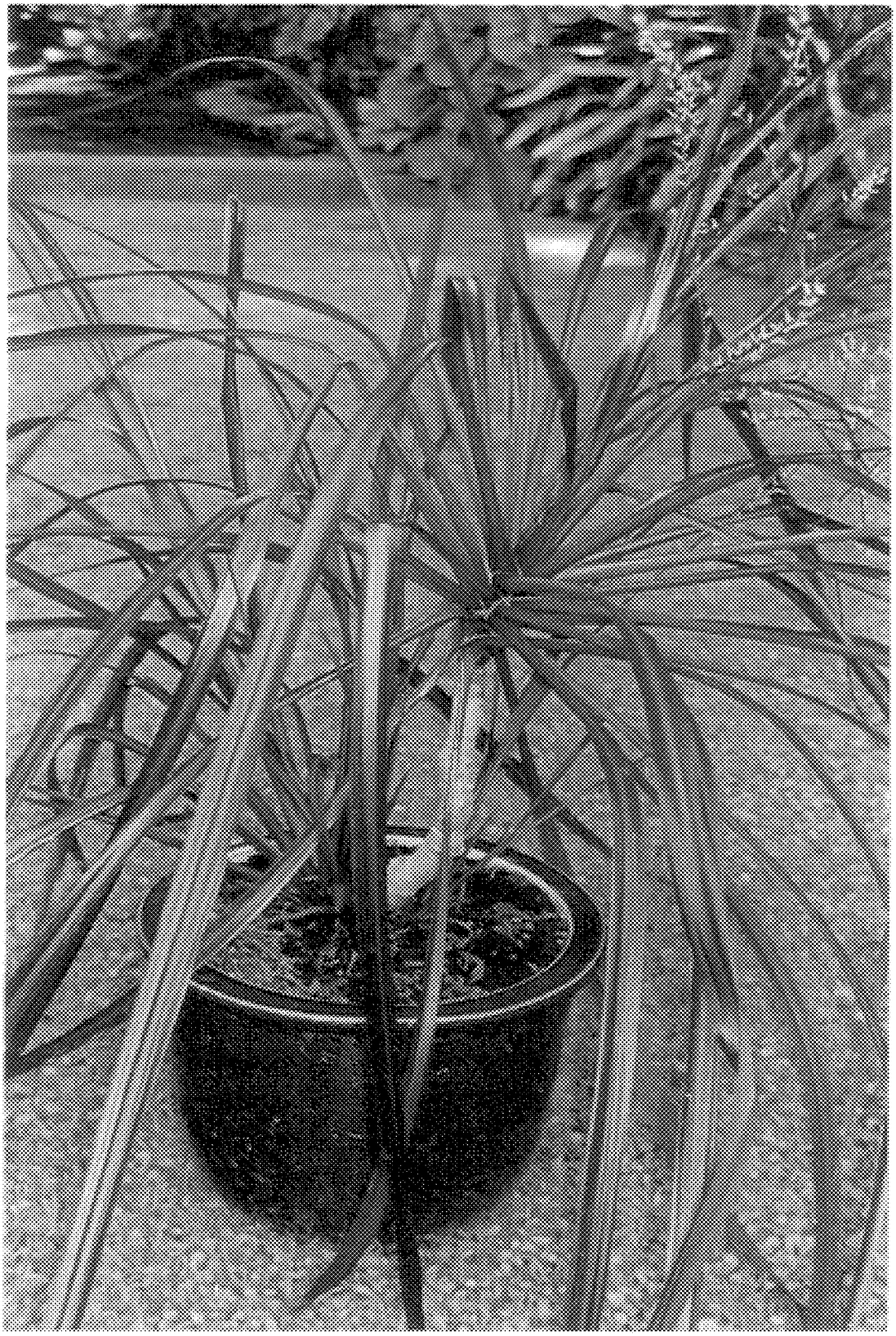

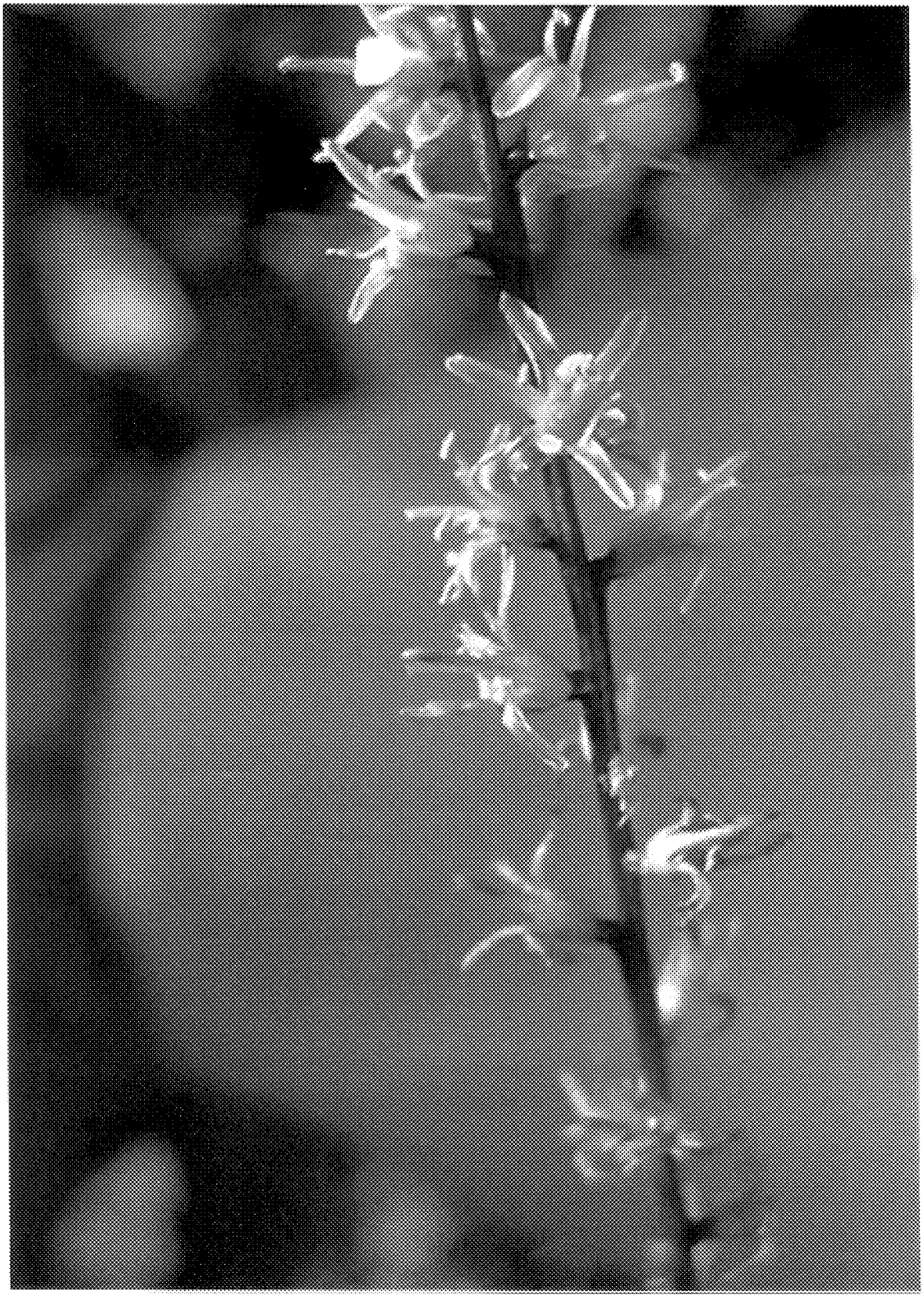

* * * * *